(12) United States Patent
Cockerill, III et al.

(10) Patent No.: US 8,101,362 B2
(45) Date of Patent: Jan. 24, 2012

(54) **DETECTION OF *CLOSTRIDIUM DIFFICILE***

(75) Inventors: Franklin R. Cockerill, III, Rochester, MN (US); Thomas F. Smith, Rochester, MN (US); Jon E. Rosenblatt, Rochester, MN (US); Lynne M. Sloan, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 229 days.

(21) Appl. No.: 12/367,014

(22) Filed: Feb. 6, 2009

(65) Prior Publication Data

US 2009/0203021 A1    Aug. 13, 2009

Related U.S. Application Data

(60) Provisional application No. 61/027,154, filed on Feb. 8, 2008.

(51) Int. Cl.
*C12Q 1/68* (2006.01)
*C12P 19/34* (2006.01)
*C07H 21/04* (2006.01)

(52) U.S. Cl. ............ 435/6.15; 435/6.12; 435/91.2; 536/24.32; 536/24.33

(58) Field of Classification Search ............ None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,824,776 A | 4/1989 | Heller | |
| 4,965,188 A | 10/1990 | Mullis et al. | |
| 4,996,143 A | 2/1991 | Heller et al. | |
| 5,035,996 A * | 7/1991 | Hartley | 435/6 |
| 5,538,848 A | 7/1996 | Livak et al. | |
| 5,565,322 A | 10/1996 | Heller | |
| 5,580,859 A | 12/1996 | Felgner et al. | |
| 5,589,466 A | 12/1996 | Felgner et al. | |
| 5,683,896 A | 11/1997 | Hartley et al. | |
| 5,702,901 A | 12/1997 | Cummins et al. | |
| 5,733,751 A | 3/1998 | Cummins et al. | |
| 5,795,717 A | 8/1998 | Nakayama et al. | |
| 5,837,452 A | 11/1998 | Clark et al. | |
| 5,849,489 A | 12/1998 | Heller | |
| 5,945,313 A | 8/1999 | Hartley et al. | |
| 6,030,115 A | 2/2000 | Ishiguro et al. | |
| 6,140,054 A | 10/2000 | Wittwer et al. | |

(Continued)

FOREIGN PATENT DOCUMENTS

KR    10-2002-0097200    12/2002

(Continued)

OTHER PUBLICATIONS

Ma, H. et al. The Journal of American Science 2(3):1-15 (2006).*

(Continued)

*Primary Examiner* — Diana Johannsen

(74) *Attorney, Agent, or Firm* — Fish & Richardson P.C.

(57) ABSTRACT

The invention provides methods to detect *C. difficile* in biological samples using real-time PCR. Primers and probes for the detection of *C. difficile* are provided by the invention. Articles of manufacture containing such primers and probes for detecting *C. difficile* are further provided by the invention.

30 Claims, 1 Drawing Sheet

U.S. PATENT DOCUMENTS

| | | | |
|---|---|---|---|
| 6,162,603 | A | 12/2000 | Heller |
| 6,174,670 | B1 | 1/2001 | Wittwer et al. |

FOREIGN PATENT DOCUMENTS

| | | |
|---|---|---|
| KR | 10-2004-0032588 | 4/2004 |
| WO | WO 84/03285 | 8/1984 |
| WO | WO 97/46707 | 12/1997 |
| WO | WO 97/46712 | 12/1997 |
| WO | WO 97/46714 | 12/1997 |
| WO | WO 01/23604 | 4/2001 |
| WO | WO 03/068918 | 8/2003 |

OTHER PUBLICATIONS

Marras, S.A.E. et al. Nucleic Acids Research 30(21):e122 (2002).*
GenBank Accession No. AM180355 dated May 13, 2009, 611 pages.
GenBank Accession No. DQ363256 dated Feb. 11, 2006, 1 page.
"LightCycler The LightCycler System," retrieved from the Internet on Sep. 28, 2001: http://biochem.roche.com/lightcycler/ , 1 page.
"LightCycler-FastStart DNA Master Hybridization Probes," 1999 Roche Diagnostics GmbH Technical Manual, retrieved from the Internet on Feb. 6, 2004 at http://www.roche-applied-science.com, 8 pages.
"LightCycler-Strep A, Primer / Hybridization Probes," Roche Applied Science Website, Jan. 3, 2002 (Retrieved from the internet on May 20, 2003—http://www.roche-applied-science.com), 1 page.
"Safety Data Sheet: LightCycler-Strep A, Primer/Hybridization Probes (ASR)," Roche Applied Science, Jan. 11, 2002, (Retrieved from the internet on May 20, 2003—http://www.roche-applied-science.com), 3 pages.
"The LightCycler™—the Smartest Innovation for More Efficient PCR," *Biochemica*, 1998, No. 2, pp. 4-7.
Abd-Elsalam, "Bioinformatic tools and guideline for PCR primer design," *African J Biotech.*, 2003, 2(5):91-95.
Aldeen et al., "Comparison of the TOX A/B test to a cell culture cytotoxicity assay for the detection of *Clostridium difficile* in stools," *Diagnostic Micro Infect Diseases*, 2000, 36:211-213.
Al-Robaiy et al., "Rapid Competitive PCR Using Melting Curve Analysis for DNA Quantification," *BioTechniques*, 2001, 31:1382-1388.
Archibald et al., "Secular trends in hospital-acquired *Clostridium difficile* disease in the United States," *J. Infect. Disease*, 2004, 189(9):1585-1589.
Ballard et al., "Comparison of Three PCR Primer Sets for Identification of *vanB* Gene Carriage in Feces and Correlation with Carriage of Vancomycin-Resistant Enterococci: Interference by *vanb*-Containing Anaerobic Bacilli," *Antimicrob Agents Chemother.*, 2005, 49(1):77-81.
Bartlett, "Antibiotic associated diarrhea," *N. Engl. J. Med.*, 2002, 346:334-339.
Bartlett, "*Clostridium difficile*: history of its role as an enteric pathogen and the current state of knowledge about the organism," *Clin. Infect. Dis.*, 1994, 18 (Suppl 4):S265-S272.
Belanger et al., "Rapid detection of *Clostridium difficile* in feces by real-time PCR," *J. Clin. Micro.*, 2003, 41(2):730-734.
Blossom and McDonald, "The challenges posed by reemerging *Clostridium difficile* Infection," *Clin. Infect. Disease*, 2007, 45(2):222-227.
Buck et al., "Design Strategies and Performance of Custom DNA Sequencing Primers," *Biotechniques*, 1999, 27:528-536.
Caplin et al., "LightCycler™ hybridization probes; The most direct way to monitor PCR amplification for quantification and mutation detection," *Biochemica*, 1999, 1:5-8.
Centers for Disease Control and Prevention. 2005. Severe *Clostridium difficle*—Associated Disease in Populations Previously at Low Risk—Four States, 2005, *MMWR*, Dec. 2, 2005, 54(47):1201-1205.
Csordas et al., "Comparison of primers for the detection of *Salmonella enterica* serovars using real-time PCR," *Lett Appl Microbiol.*, 2004, 39:187-193.
Curry et al., "tcdC Genotypes associated with severe TcdC truncation in an epidemic clone and other strains of *Clostridium dififcile*," *J. Clin. Micro.*, 2007, 45:215-221.
De Silva et al., "Rapid Genotyping and Quantification on the LightCycler with Hybridization Probes," *Biochemica*, 1998, 2:12-15.
Didenko, "DNA Probes Using Fluorescence Resonance Energy Transfer (FRET): Designs and Applications," *BioTechniques*, 2001, 31:1106-1121.
Elnifro et al., "Multiplex PCR: Optimization and Application in Diagnostic Virology," *Clin Microbiol Rev*, 2000, 13(4):559-570.
Gaynes et al., "Outbreak of *Clostridium difficile* Infection in a long-term care facility: association with gatifloxacin use," *Clin. Infect. Dis.*, 2004, 38(5):640-645.
Geric et al., "Binary toxin-producing, large clostridial toxin-negative *Clostridium difficile* strains are enterotoxic but do not cause disease in humans," *J. Infect. Diseases*, 2006, 193(8):1143-1150.
Higuchi et al., "Simultaneous Amplification and Detection of Specific DNA Sequences," *Bio/Technology*, 1992, 40:413-417.
Hillier and Green, "OSP: a computer program for choosing PCR and DNA sequencing primers," *PCR Meth Appl.*, 1991, 1:124-128.
Livak et al., "Oligonucleotides with Fluorescent Dyes at Opposite Ends Provide A Quenched Probe System Useful for Detecting PCR Product and Nucleic Acid Hybridization," *Genome Research*, 1995, 4:357-362.
Longo et al., "Use of uracil DNA glycosylase to control carry-over contamination in polymerase chain reactions," *Gene*, 1990, 93:125-128.
Loo et al., "A predominately clonal multi-institutional outbreak of *Clostridium difficile-associated* diarrhea with high morbidity and mortality," *N. Engl. J. Med.*, 2005, 353(23):2442-2449.
Lowe et al., "A computer program for selection of oligonucleotide primers for polymerase chain reactions," *Nuc. Acids Res.*, 1990, 18(7):1757-61.
Matamouros et al., "*Clostridium difficile* toxin expression is inhibited by the novel regulator TcdC," *Mol. Microbiology*, 2002, 64(5):1274-1288.
McDonald et al., "An epidemic, toxin gene-variant strain of *Clostridium difficile*," *N. Engl. J. Med.*, 2005, 353(23):2433-2441.
McDonald et al., "*Clostridium difficile* infection in patients discharged from US short-stay hospitals, 1996-2003," *Emerg. Infect. Diseases*, 2006, 12(3):409-415.
McEllistrem et al., "A hospital outbreak of *Clostridium difficile* disease associated with isolates carrying binary toxin genes," *Clin. Infect. Dis.*, 2005, 40(2):265-272.
Musher et al., "Detection of *Clostridium difficile* Toxin: comparison of enzyme immunoassay results with results obtained by cytotoxicity assay," *J. Clin. Micro.*, 2007, 45(8):2737-2739.
Muto et al., "A large outbreak of *Clostridium difficile-associated* disease with an unexpected proportion of deaths and colectomies at a teaching hospital following increased fluoroquinolone use," *Infect. Control Hosp. Epidemiol.*, 2005, 26(3):273-280.
Peterson and Kelly, "The role of the clinical microbiology laboratory in the management of *Clostridium difficile-associated* diarrhea," *Infect. Diseases Clinics of North America*, 1993, 7:277-293.
Peterson et al., "Detection of toxigenic *Clostridium difficile* in stool samples by real-time polymerase chain reaction for the diagnosis of *C. difficile*-associated diarrhea," *Clin. Infect. Dis.*, 2007, 45(9):1152-1160.
Peterson et al., "Results of a prospective, 18-month clinical evaluation of culture, cytotoxin testing, and culturette brand (CDT) latex testing in the diagnosis of *Clostridium difficile*-associated diarrhea," *Diagn. Microbiol. Infect. Dis.*, 1988, 10(2):85-91.
Razavi et al., "*Clostridium difficile*: Emergence of hypervirulence and fluroquinolone resistance," *Infection*, 2007, 35(5):300-307.
Redelings et al., "Increase in *Clostridium difficile-related* morality rates, United States, 1999-2004," *Emerg. Infect. Diseases*, 2007, 13(9):1417-1419.
Spigaglia and Mastrantonio, "Molecular analysis of the Pathogenicity Locus and Polymorphism in the Putative Negative Regulator of Toxin Production (TcdC) among *Clostridium difficile* clinical isolates," *J. Clin. Micro.*, 2002, 40(9):3470-3475.

Terhes et al., "Community-acquired *Clostridium difficile* diarrhea caused by binary toxin, toxin A, and toxin B gene-positive isolates in Hungary," *J. Clin. Micro.*, 2004, 42(9):4316-4318.

Ticehurst et al., "Effective detection of toxigenic *Clostridium difficile* by a twostep algorithm including tests for antigen and cytotoxin," *J. Clin. Micro.*, 2006, 44:1145-1149.

Tichopad et al., "Inhibition of real-time RT-PCR quantification due to tissue-specific contaminants," *Mol Cell Probes*, 2004, 18:45-50.

Turgeon et al., "Six rapid tests for direct detection of *Clostridium difficile* and its toxins in fecal samples compared with the fibroblast cytotoxicity assay," *J. Clin. Micro.*, 2003, 41(2):667-670.

Van Den Berg et al., "Evaluation of real-time PCR and conventional diagnostic methods for the detection of *Clostridium difficile* associated diarrhea in a prospective multicentre study," *J. Med. Micro.*, 2007, 56(Pt 1):36-42.

Warny et al., "Toxin production by an emerging strain of *Clostridium difficile* associated with outbreaks of severe disease in North America and Europe," *Lancet*, 2005, 366(9491):1079-1084.

Wilkins and Lyerly, "*Clostridium difficile* Testing: after 20 years, still challenging," *J. Clin. Micro.*, 2003, 41(2):531-534.

Wittwer et al., "Continuous Fluorescence Monitoring of Rapid Cycle DNA Amplification," *Biotechniques*, 1997, 22:130-138.

Zar et al., "A comparison of vancomycin and metronidazole for the treatment of *Clostridium difficile*-associated diarrhea, stratified by disease severity," *Clin. Infect. Dis.*, 2007, 45(3):302-307.

Authorized Officer Kee-Yeum Kim, International Search Report in PCT/US2009/033215 mailed Sep. 21, 2009, 4 pages.

Authorized Officer Kee-Yeum Kim, Written Opinion of the International Searching Authority for PCT/US2009/033215 mailed Sep. 21, 2009, 4 pages.

Authorized Officer Beate Giffo-Schmitt, International Preliminary Report on Patentability for PCT/US2009/033215 issued Oct. 10, 2010, 5 pages.

European Patent Office, Supplemental European Search Report, EP 09 70 8257, dated Apr. 26, 2011, 9 pages.

Sloan, L.M., et al. Comparison of real-time PCR bacterial culture, and five commercial assays for the detection of *Clostridium difficile* Toxins in Stool samples: *Abstracts of the General Meeting of the American Society for Microbiology*, vol. 107, 2007, p. 188 & *107th General Meeting of the American-Society -For-Microbiology*, Toronto, Canada; 2007.

Killgore, George et al. "Comparison of seven techniques for typing international epidemic strains of *Clostridium difficile*: restriction enodnuclease analysis, pusled-field gel electrophoresis, PCR-ribotyping, multilocus sequence typing, multilocus variable-number tandem-repeat analysis, amplified fragment length polymorphisms" *Journal of Clinical Microbiology*, vol. 46, No. 2, Nov. 26, 2007, pp. 431-437.

Wroblewski, D. et al. "Diagnosis and characterization of *Clostridium difficile* using multiplex real-time PCR and sequence analysis" *Abstracts of the General Meeting of the American Society for Biology*, vol. 107, Jan. 1, 2007, p. 211, The Society, Washington, DC, US.

Hookman, P. et al. "Review: *Clostridium difficile* -Associated Disorders/Diarrhea and *Clostridium difficile* Colitis: The Emergence of a More Virulent Era" *Digestive Diseases and Sciences*, vol. 52, No. 4, Feb. 16, 2007, pp. 1071-1075.

Sloan, L.M., et al. "Comparison of real-time PCR for detection of the tcdC gene with four toxin immunoassays and culture in diagnosis of *Clostridium difficile* infection" *Journal of Clinical Microbiology*, vol. 45, No. 6, Jun. 1, 2008, pp. 1996-2001.

* cited by examiner

US 8,101,362 B2

SEQUENCE LISTING

<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide

<400> SEQUENCE: 1
acctcatcac catcttcaat aac                                          23

<210> SEQ ID NO 2
<211> LENGTH: 21
<212> TYPE: DNA
<213> ORGANISM: Artificial Sequence

```
<220> FEATURE:
<223> OTHER INFORMATION: Oligonucleotide

<400> SEQUENCE: 2
tcaaaatgaa agacgacgaa a                                              21

<210> SEQ ID NO 3
<211> LENGTH: 24
<212> TYPE: DNA
<213> ORGANISM: Artificial Sequence
<220> FEATURE:
<223> OTHER INFORMATION: Oligonucleotide

<400> SEQUENCE: 3
ttcagccttt ttagcttctt cagc                                           24

<210> SEQ ID NO 4
<211> LENGTH: 26
<212> TYPE: DNA
<213> ORGANISM: Artificial Sequence
<220> FEATURE:
<223> OTHER INFORMATION: Oligonucleotide

<400> SEQUENCE: 4
ttacgttgat tttcagcttc aatagc                                         26

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide

<400> SEQUENCE: 5
gagctgcttc aattggagag a                                              21

<210> SEQ ID NO 6
<211> LENGTH: 23
<212> TYPE: DNA
<213> ORGANISM: Artificial Sequence
<220> FEATURE:
<223> OTHER INFORMATION: Oligonucleotide

<400> SEQUENCE: 6
gtaacctact ttcataacac cag                                            23

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide

<400> SEQUENCE: 7
atgataaggc aacttcagtg g                                              21

<210> SEQ ID NO 8
<211> LENGTH: 22
<212> TYPE: DNA
<213> ORGANISM: Artificial Sequence
<220> FEATURE:
<223> OTHER INFORMATION: Oligonucleotide

<400> SEQUENCE: 8
taagttcctc ctgctccatc aa                                             22
```

```
<210> SEQ ID NO 9
<211> LENGTH: 20
<212> TYPE: DNA
<213> ORGANISM: Artificial Sequence
<220> FEATURE:
<223> OTHER INFORMATION: Oligonucleotide

<400> SEQUENCE: 9
tgaacctgga aaaggtgatg                                               20

<210> SEQ ID NO 10
<211> LENGTH: 23
<212> TYPE: DNA
<213> ORGANISM: Artificial Sequence
<220> FEATURE:
<223> OTHER INFORMATION: Oligonucleotide

<400> SEQUENCE: 10
aggattattt actggaccat ttg                                           23

<210> SEQ ID NO 11
<211> LENGTH: 22
<212> TYPE: DNA
<213> ORGANISM: Artificial Sequence
<220> FEATURE:
<223> OTHER INFORMATION: Oligonucleotide

<400> SEQUENCE: 11
cttaatgcaa gtaaatactg ag                                            22

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide

<400> SEQUENCE: 12
aacggatctc ttgcttcagt c                                             21
```

DETECTION OF CLOSTRIDIUM DIFFICILE

CROSS REFERENCE TO RELATED APPLICATIONS

This application claims priority under 35 U.S.C. §119(e) of U.S. provisional application Ser. No. 61/027,154, filed Feb. 8, 2008.

TECHNICAL FIELD

This invention relates to microbial diagnostics, and more particularly to the detection of Clostridium difficile.

BACKGROUND

Clostridium difficile is the most common identified cause of antibiotic associated diarrhea, accounting for 15%-25% of cases (Bartlett, 1994, Clin. Infect. Dis., 18 (Suppl 4): S265-272). C. difficile infection (CDI) encompasses a wide range of clinical syndromes from simple diarrhea to pseudomembranous colitis associated with significant morbidity and mortality. There has been a marked increase in the incidence and severity of CDI in recent years, and in 2001, there was a 42% increase in U.S. short-stay hospital discharge diagnoses of CDI. There was a further increase of 25% between 2003 and 2004 and another 10% in 2005. The increase was greatest in patients>64 years of age and occurred in most geographic areas of the country. C. difficile-related mortality rates per million of United States population rose from 5.7 in 1999 to 23.7 in 2004, and there were an estimated 26,642 deaths due to CDI during 1999-2004.

In 2000, a more severe form of CDI was identified in the U.S. and Canada and also in Europe. Many cases of this severe form of CDI have been shown to be caused by an "epidemic" strain of C. difficile, which has been characterized as "BI" by restriction enzyme analysis (REA), "NAP1" (North American Pulsed Field Type 1) by pulsed field gel electrophoresis, and "027" by PCR ribotyping. In addition, it has been characterized as "toxinotype III" (by REA of toxin genes). In prior years, the great majority of "non-epidemic" hospital strains of C. difficile belonged to toxinotype 0. This BI/NAP1/027 "epidemic" strain has been shown to be a hyperproducer of toxins A and B, which may be the primary reason for the increased virulence of the epidemic strain. The tcdC gene, within the pathogenicity locus of the "epidemic" strain, appears to be a negative regulator of toxin A and B production.

SUMMARY

The invention provides for methods of identifying Clostridium difficile nucleic acid by real-time polymerase chain reaction (PCR) in a biological sample. Primers and probes for detecting C. difficile are provided by the invention, as are kits containing such primers and probes. Methods of the invention can be used to rapidly identify C. difficile nucleic acid from specimens for diagnosis of C. difficile infection. Using specific primers and probes, the methods include amplifying and monitoring the development of specific amplification products using fluorescence resonance energy transfer (FRET).

In one aspect, the invention provides for methods of detecting the presence or absence of C. difficile in a biological sample from an individual. Such methods generally include performing at least one cycling step, which includes an amplifying step and a hybridizing step. Typically, the amplifying step includes contacting the sample with a pair of tcdC primers to produce a tcdC amplification product if a tcdC nucleic acid molecule is present in the sample, and the hybridizing step includes contacting the sample with a pair of tcdC probes. The members of the pair of tcdC probes generally hybridize within no more than five nucleotides of each other (e.g., no more than two nucleotides of each other, no more than one nucleotide of each other) and a first tcdC probe of the pair of tcdC probes is labeled with a donor fluorescent moiety while a second tcdC probe of the pair of tcdC probes is labeled with a corresponding acceptor fluorescent moiety. Such methods also include detecting the presence or absence of fluorescence resonance energy transfer (FRET) between the donor fluorescent moiety of the first tcdC probe and the acceptor fluorescent moiety of the second tcdC probe, wherein the presence of FRET is indicative of the presence of C. difficile in the sample, and wherein the absence of FRET is indicative of the absence of C. difficile in the sample.

Generally, the pair of tcdC primers includes a first tcdC primer and a second tcdC primer, wherein the first tcdC primer comprises or consists of the sequence 5'-ACC TCA TCA CCA TCT TCA ATA AC-3' (SEQ ID NO:1) and the second tcdC primer comprises or consists of the sequence 5'-TCA AAA TGA AAG ACG ACG AAA-3' (SEQ ID NO:2). Generally, the first tcdC probe comprises or consists of the sequence 5'-TTC AGC CTT TTT AGC TTC TTC AGC-3' (SEQ ID NO:3) and the second tcdC probe comprises or consists of the sequence 5'-TTA CGT TGA TTT TCA GCT TCA ATA GC-3' (SEQ ID NO:4).

A representative donor fluorescent moiety is fluorescein, and representative corresponding acceptor fluorescent moieties include LC-Red 640, LC-Red 705, Cy5, and Cy5.5. Typically, the detecting step includes exciting the sample at a wavelength absorbed by the donor fluorescent moiety and visualizing and/or measuring the wavelength emitted by the corresponding acceptor fluorescent moiety. In some embodiments, the detecting includes quantitating the FRET. In some embodiments, the detecting step is performed after each cycling step. In certain embodiments, the detecting step is performed in real time.

The methods disclosed herein can further include determining the melting temperature between one or both of the tcdC probe(s) and the tcdC amplification product. As described herein, the melting temperature confirms the presence or absence of C. difficile. In certain instances, the determining results in two separate melting temperatures, which is indicative of wild type C. difficile. In other instances, the determining results in only one melting temperature, which is indicative of a C. difficile mutant that contains a genetic deletion (e.g., an 18 bp deletion or a 39 bp deletion) in the tcdC nucleic acid sequence.

In some embodiments, the methods disclosed herein further include: preventing amplification of a contaminant nucleic acid. In certain instances, such a preventing step includes performing the amplifying step in the presence of uracil and then treating the sample with uracil-DNA glycosylase prior to the first amplifying step.

Representative biological samples include, without limitation, a stool sample, a peri-anal sample, or a rectal sample. The methods described herein (i.e., a cycling step) can be performed on a control sample. In some embodiments, the control sample comprises a portion of the tcdC nucleic acid molecule. In other embodiments, the cycling step uses a pair of control primers and a pair of control probes that are other than the tcdC primers and tcdC probes. Under these circumstances, the amplifying step produces a control amplification product, and the control probes hybridize to the control amplification product.

In another aspect, the invention provides methods for detecting the presence or absence of *C. difficile* in a biological sample from an individual. Such methods generally include performing at least one cycling step, which typically includes an amplifying step and a hybridizing step. Generally, the amplifying step includes contacting the sample with a pair of tcdC primers to produce a *C. difficile* tcdC amplification product if a tcdC nucleic acid molecule is present in the sample and the hybridizing step includes contacting the sample with a tcdC probe that is labeled with a donor fluorescent moiety and a corresponding acceptor fluorescent moiety. Such methods also include detecting the presence or absence of fluorescence resonance energy transfer (FRET) between the donor fluorescent moiety and the acceptor fluorescent moiety of the tcdC probe, wherein the presence or absence of fluorescence is indicative of the presence or absence of *C. difficile* in the sample.

In some embodiments of these methods, the amplification can employ a polymerase enzyme having 5' to 3' exonuclease activity and the second fluorescent moiety can be a quencher. In other embodiments, the tcdC probe can include a nucleic acid sequence that permits secondary structure formation, wherein the secondary structure formation results in spatial proximity between the first and second fluorescent moiety and the second fluorescent moiety can be a quencher. According to the methods described herein, the first and second fluorescent moieties typically are within no more than 5 nucleotides of each other on the probe.

In still another aspect, the invention provides for methods of detecting the presence or absence of *C. difficile* in a biological sample from an individual. Such methods generally include performing at least one cycling step, which includes an amplifying step and a dye-binding step. Typically, the amplifying step includes contacting the sample with a pair of tcdC primers to produce a tcdC amplification product if a tcdC nucleic acid molecule is present in the sample and the dye-binding step includes contacting the tcdC amplification product with a double-stranded DNA binding dye. Such methods also include detecting the presence or absence of binding of the double-stranded DNA binding dye into the amplification product, wherein the presence of binding is indicative of the presence of *C. difficile* in the sample, and wherein the absence of binding is indicative of the absence of *C. difficile* in the sample. A representative double-stranded DNA binding dye is ethidium bromide. In addition, such methods also can include determining the melting temperature between the tcdC amplification product and the double-stranded DNA binding dye, wherein the melting temperature confirms the presence or absence of the *C. difficile*.

In another aspect, the invention provides for articles of manufacture that include a pair of tcdC primers; a pair of tcdC probes; and a donor fluorescent moiety and a corresponding acceptor fluorescent moiety. Typically, the pair of tcdC primers includes a first tcdC primer and a second tcdC primer, wherein the first tcdC primer comprises or consists of the sequence 5'-ACC TCA TCA CCA TCT TCA ATA AC-3' (SEQ ID NO:1) and the second tcdC primer comprises of consists of the sequence 5'-TCA AAA TGA AAG ACG ACG AAA-3' (SEQ ID NO:2). Typically, the pair of tcdC probes includes a first tcdC probe and a second tcdC probe, wherein the first tcdC probe comprises or consists of the sequence 5'-TTC AGC CTT TTT AGC TTC TTC AGC-3' (SEQ ID NO:3) and wherein the second tcdC probe comprises or consists of the sequence 5'-TTA CGT TGA TTT TCA GCT TCA ATA GC-3' (SEQ ID NO:4).

In certain embodiments, the first tcdC probe is labeled with the donor fluorescent moiety and the second tcdC probe is labeled with the corresponding acceptor fluorescent moiety within the article of manufacture. In addition, an article of manufacture as described herein also has a package insert having instructions thereon for using the pair of tcdC primers and the pair of tcdC probes to detect the presence or absence of *C. difficile* in a sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION

Figure 1:
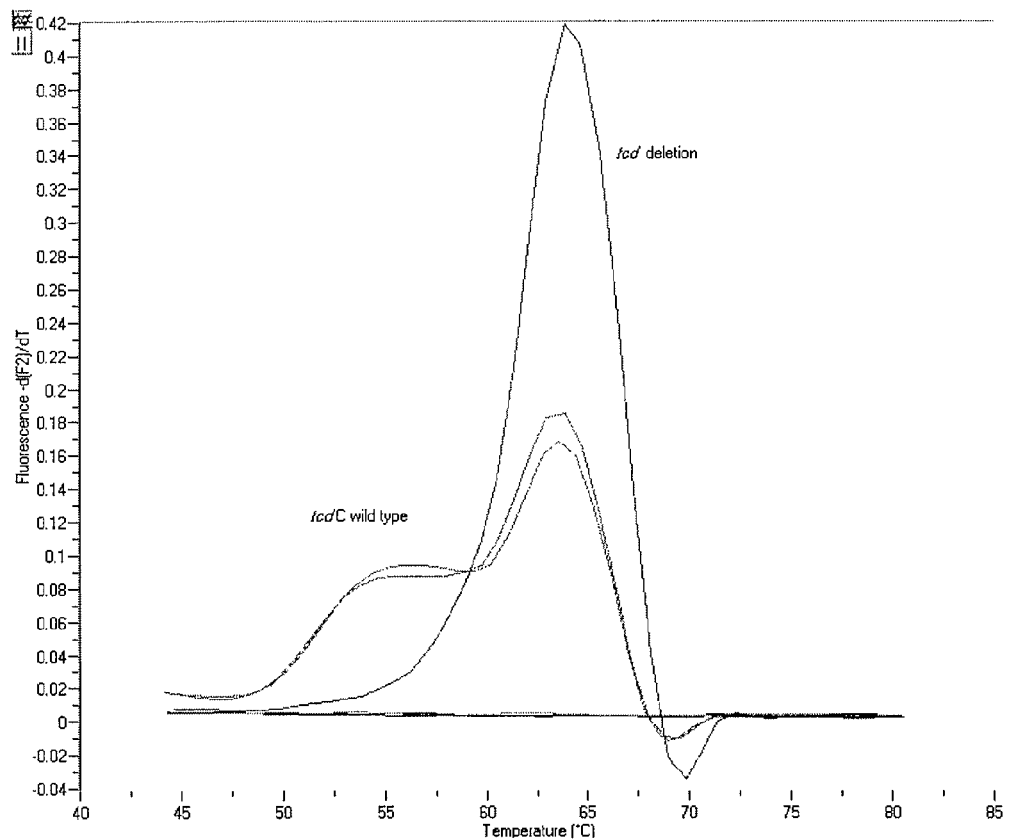
FIG. 1 is a graph showing the results of LIGHTCYCLER PCR of *C. difficile* tcdC gene showing the melt temperature patterns of the "wild type" strain (no deletions present) and a strain in which deletions were present.

A real-time assay for detecting *Clostridium difficile* in a biological sample that is more sensitive and specific than existing assays is described herein. Primers and probes for detecting *C. difficile* infections and articles of manufacture containing such primers and probes are provided by the invention. The increased sensitivity of real-time PCR for detection of *C. difficile* compared to other methods, as well as the improved features of real-time PCR including sample containment and real-time detection of the amplified product, make feasible the implementation of this technology for routine diagnosis of *C. difficile* infections in the clinical laboratory.

*C. difficile* Nucleic Acids and Oligonucleotides

The invention provides methods to detect *C. difficile* by amplifying, for example, a portion of a tcdC nucleic acid. tcdC nucleic acid sequences from *C. difficile* are available in, for example, in public databases. See, for example, GenBank Accession No. DQ363256 for the sequence of the tcdC gene, and GenBank Accession Nos. NC_009089 and AM180355.

Specifically, primers and probes to amplify and detect *C. difficile* nucleic acid molecules are provided by the invention. *C. difficile* nucleic acids other than those exemplified herein also can be used to detect *C. difficile* in a sample. *C. difficile* nucleic acids other than those exemplified herein (e.g., functional variants) can be evaluated (e.g., for specificity and/or sensitivity) by those of skill in the art using routine methods such as, but not limited to, the methods exemplified herein.

Representative functional variants, for example, include deletions of, insertions in, and/or substitutions in the nucleic acids disclosed herein.

Primers that amplify an *C. difficile* nucleic acid molecule, e.g., *C. difficile* can be designed using, for example, a computer program such as OLIGO (Molecular Biology Insights, Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 15 to 30 (e.g., 16, 18, 20, 21, 22, 23, 24, or 25) nucleotides in length.

Designing oligonucleotides to be used as hybridization probes can be performed in a manner similar to the design of primers, although the members of a pair of probes preferably anneal to an amplification product within no more than 5 nucleotides of each other on the same strand such that FRET can occur (e.g., within no more than 1, 2, 3, or 4 nucleotides of each other). This minimal degree of separation typically brings the respective fluorescent moieties into sufficient proximity such that FRET occurs. It is to be understood, however, that other separation distances (e.g., 6 or more nucleotides) are possible provided the fluorescent moieties are appropriately positioned relative to each other (for example, with a linker arm) such that FRET can occur. In addition, probes can be designed to hybridize to targets that contain a polymorphism or mutation, thereby allowing differential detection of *C. difficile* strains based on either absolute hybridization of different pairs of probes corresponding to the particular *C. difficile* strain to be distinguished or differential melting temperatures between, for example, members of a pair of probes and each amplification product corresponding to an *C. difficile* strain to be distinguished. As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are generally 15 to 30 (e.g., 16, 18, 20, 21, 22, 23, 24, or 25) nucleotides in length.

Constructs of the invention include vectors containing a *C. difficile* nucleic acid molecule (e.g., SEQ ID NOs:1, 2, 3, or 4). Constructs of the invention can be used, for example, as control template nucleic acid molecules. Vectors suitable for use in the present invention are commercially available and/or produced by recombinant nucleic acid technology methods routine in the art. *C. difficile* nucleic acid molecules can be obtained, for example, by chemical synthesis, direct cloning from *C. difficile*, or by PCR amplification. A *C. difficile* nucleic acid molecule or fragment thereof can be operably linked to a promoter or other regulatory element such as an enhancer sequence, a response element, or an inducible element that modulates expression of the *C. difficile* nucleic acid molecule. As used herein, operably linking refers to connecting a promoter and/or other regulatory elements to a *C. difficile* nucleic acid molecule in such a way as to permit and/or regulate expression of the *C. difficile* nucleic acid molecule. A promoter that does not normally direct expression of *C. difficile* can be used to direct transcription of a *C. difficile* nucleic acid using, for example, a viral polymerase, a bacterial polymerase, or a eukaryotic RNA polymerase II. Alternatively, the *C. difficile* native promoter can be used to direct transcription of a *C. difficile* nucleic acid. In addition, operably linked can refer to an appropriate connection between a *C. difficile* promoter or regulatory element and a heterologous coding sequence (i.e., a non-*C. difficile* coding sequence, for example, a reporter gene) in such a way as to permit expression of the heterologous coding sequence.

Constructs suitable for use in the methods of the invention typically include, in addition to *C. difficile* nucleic acid molecules (e.g., a nucleic acid molecule that contains one or more sequences of SEQ ID NOs:1, 2, 3, or 4), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs of the invention containing *C. difficile* nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens* and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct of the invention can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in the present invention include oligonucleotides capable of acting as a point of initiation of nucleic acid synthesis within *C. difficile* nucleic acid sequences (e.g., SEQ ID NO:1, 2, 3, or 4). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus fiavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence on the *C. difficile* nucleic acid. The temperature for annealing is usually from about 35° C. to about 65° C. (e.g., about 40° C. to about 60° C.; about 45° C. to about 50° C.). Annealing times can be from about 10 secs to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° to 80° C. (e.g., about 50° C. to about 70° C.; about 60° C.). Extension times can be from about 10 secs to about 5 mins (e.g., about 30 sec to about 4 min; about 1 min to about 3 min; about 1 min 30 sec to about 2 min).

PCR assays can employ *C. difficile* nucleic acid such as RNA or DNA (cDNA). The template nucleic acid need not be purified; it may be a minor fraction of a complex mixture, such as *C. difficile* nucleic acid contained in human cells. *C. difficile* nucleic acids may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers (e.g., SEQ ID NO:1 or 2) are combined with PCR reagents under reaction conditions that induce primer extension. For example, chain extension reactions generally include 50 mM KCl, 10 mM Tris-HCl (pH 8.3), 15 mM MgCl$_2$, 0.001% (w/v) gelatin, 0.5-1.0 μg denatured template DNA, 50 pmoles of each oligonucleotide primer, 2.5 U of Taq polymerase, and 10% DMSO). The reactions usually contain 150 to 320 μM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target *C. difficile* nucleic acid molecule. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor and a corresponding acceptor fluorescent moiety are positioned within a certain distance of each other, energy transfer takes place between the two fluorescent moieties that can be visualized or otherwise detected and/or quantitated. Two oligonucleotide probes (e.g., SEQ ID NO:3 or 4), each containing a fluorescent moiety, can hybridize to an amplification product at particular positions determined by the complementarity of the oligonucleotide probes to the *C. difficile* target nucleic acid sequence. Upon hybridization of the oligonucleotide probes to the amplification product nucleic acid at the appropriate positions, a FRET signal is generated. Hybridization temperatures can range from about 35° C. to about 65° C. (e.g., about 40° C. to about 60° C.; about 45° C. to about 55° C.; about 50° C.) for about 10 sec to about 1 min (e.g., about 20 sec to about 50 sec; about 30 sec to about 40 sec).

Fluorescent analysis can be carried out using, for example, a photon counting epifluorescent microscope system (containing the appropriate dichroic mirror and filters for monitoring fluorescent emission at the particular range), a photon counting photomultiplier system or a fluorometer. Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties "corresponding" refers to an acceptor fluorescent moiety having an emission spectrum that overlaps the excitation spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Förster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimidyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC™-Red 640, LC™-Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm for the purpose of the present invention is the distance in Angstroms (Å) from the nucleotide base to the fluorescent moiety. In general, a linker arm is from about 10 to about 25 Å (e.g., about 15 Å to about 20 Å). The linker arm may be of the kind described in WO 84/03285. WO 84/03285 also discloses methods for attaching linker arms to a particular nucleotide base, and also for attaching fluorescent moieties to a linker arm.

An acceptor fluorescent moiety such as an LC™-Red 640-NHS-ester can be combined with C6-Phosphoramidites (available from ABI (Foster City, Calif.) or Glen Research (Sterling, Va.)) to produce, for example, LC™-Red 640-Phosphoramidite. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, ester-derived, such as fluorescein-CPG from BioGenex (San Ramon, Calif.)), or 3'-amino-CPG's that require coupling of a fluorescein-NHS-ester after oligonucleotide synthesis.

Detection of *C. difficile*

Cytotoxicity of stools toward a variety of tissue cell lines (CTX) was the initial method used to detect *C. difficile* and has been viewed by some as the "gold standard" (Musher et al., 2007, *J. Clin. Micro.*, 45:2737-9). However, this assay relies upon subjective interpretation of cytotoxicity by technologists, requires a neutralization step using specific antiserum, has a long turn-around time, and is not commercially available. Thus, CTX is little used today by diagnostic laboratories.

Anaerobic culture of stools on selective and differential media (CCFA) is more sensitive than CTX but is complex, time consuming, and requires confirmation of toxigenicity of isolates by another method (Peterson and Kelly, 1993, *Infect. Diseases Clinics of North America*, 7:277-93).

Direct detection of the antigens of toxins A, B, or both by a variety of commercially produced EIAs is rapid and simple and is the method most widely used now by clinical laboratories. Several studies reported ≧90% sensitivity of EIAs when compared to CTX. Since the latter is only 70%-80% as sensitive as culture (the "real gold standard"), however, the true sensitivity of the EIAs is much lower than 90% and has been reported to be as low as 70%.

An additional commercially available assay that detects glutamate dehydrogenase (GDH), known as the "common antigen" of *C. difficile*, is viewed by some as a surrogate method for culture. This assay does not differentiate toxigenic and non-toxigenic strains, however, and is therefore not suitable as a single diagnostic test for CDI.

Several laboratories have reported the use of real-time polymerase chain reaction (PCR) methods directly on stool specimens for the diagnosis of CDI. These assays targeted the genes associated with toxin B (tcdB) or both toxins A and B (tcdA and tcdB) and showed a high concordance with results from either CTX or toxigenic culture. However, none of these assays allowed one to identify the presence of the "epidemic" or BI strain of *C. difficile* at the same time.

By using commercially available real-time PCR instrumentation (e.g., LIGHTCYCLER™, Roche Molecular Biochemicals, Indianapolis, Ind.), however, PCR amplification and detection of the amplification product can be combined in a single closed cuvette with dramatically reduced cycling time. Since detection occurs concurrently with amplification, the real-time PCR methods obviate the need for manipulation of the amplification product, and diminish the risk of cross-contamination between amplification products. Real-time PCR greatly reduces turn-around time and is an attractive alternative to conventional PCR techniques in the clinical laboratory.

The present invention provides methods for detecting the presence or absence of *C. difficile* in a biological sample from an individual. Methods provided by the invention avoid problems of sample contamination, false negatives, and false positives. The methods can be used to determine whether or not a patient is in need of treatment for *C. difficile*. If positive, the patient can be administered an appropriate medication (e.g., metronidazole or vancomycin) in a timely manner.

The methods include performing at least one cycling step that includes amplifying a portion of a *C. difficile* nucleic acid molecule from a sample using a pair of *C. difficile* primers. Each of the *C. difficile* primers anneals to a target within or adjacent to a *C. difficile* nucleic acid molecule such that at least a portion of each amplification product contains nucleic acid sequence corresponding to *C. difficile*. More importantly, the amplification product should contain the nucleic acid sequences that are complementary to the *C. difficile* probes. The *C. difficile* amplification product is produced provided that *C. difficile* nucleic acid is present. Each cycling step further includes contacting the sample with a pair of *C. difficile* probes. According to the invention, one member of each pair of the *C. difficile* probes is labeled with a donor fluorescent moiety and the other is labeled with a corresponding acceptor fluorescent moiety. The presence or absence of FRET between the donor fluorescent moiety of the first *C. difficile* probe and the corresponding acceptor fluorescent moiety of the second *C. difficile* probe is detected upon hybridization of the *C. difficile* probes to the *C. difficile* amplification product.

Each cycling step includes an amplification step and a hybridization step, and each cycling step is usually followed by a FRET detecting step. Multiple cycling steps are performed, preferably in a thermocycler. Methods of the invention can be performed using a *C. difficile* primer and probe set to detect the presence of *C. difficile*. Detection of FRET in the *C. difficile* reaction indicates the presence of *C. difficile*.

As used herein, "amplifying" refers to the process of synthesizing nucleic acid molecules that are complementary to one or both strands of a template nucleic acid molecule (e.g., *C. difficile* nucleic acid molecules). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., PLATINUM® Taq) and an appropriate buffer and/or co-factors for optimal activity of the polymerase enzyme (e.g., $MgCl_2$ and/or KCl).

If amplification of *C. difficile* nucleic acid occurs and an amplification product is produced, the step of hybridizing results in a detectable signal based upon FRET between the members of the pair of probes. As used herein, "hybridizing"

refers to the annealing of probes to an amplification product. Hybridization conditions typically include a temperature that is below the melting temperature of the probes but that avoids non-specific hybridization of the probes.

Generally, the presence of FRET indicates the presence of *C. difficile* in the sample, and the absence of FRET indicates the absence of *C. difficile* in the sample. Inadequate specimen collection, transportation delays, inappropriate transportation conditions, or use of certain collection swabs (e.g., calcium alginate swabs or aluminum shaft swabs) are all conditions that can affect the success and/or accuracy of a test result, however. Using the methods disclosed herein, detection of FRET within 45 cycling steps is indicative of a *C. difficile* infection.

Methods of the invention also can be used for *C. difficile* vaccine efficacy studies or epidemiology studies. For example, a *C. difficile* vaccine can be detected using the methods of the invention during the time when the inocula is still present in an individual. For such vaccine efficacy studies, the methods of the invention can be used to determine, for example, the persistence of an attenuated strain of *C. difficile* used in a vaccine, or can be performed in conjunction with an additional assay such as a serologic assay to monitor an individual's immune response to such a vaccine. In addition, methods of the invention can be used to distinguish one *C. difficile* strain from another for epidemiology studies of, for example, the origin or severity of an outbreak of *C. difficile*. In addition, monitoring how long *C. difficile* persists in an infected patient enables hospital infection control teams to limit and possibly reduce nosocomial transmission.

Representative biological samples that can be used in practicing the methods of the invention include, without limitation, stool samples, peri-anal samples, or rectal samples. Collection and storage methods of biological samples are known to those of skill in the art. Biological samples can be processed (e.g., by nucleic acid extraction methods and/or kits known in the art) to release *C. difficile* nucleic acid or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the tcdC probes from the tcdC amplification product can confirm the presence or absence of *C. difficile* in the sample. Using the probes having SEQ ID NOs:3 and 4 as disclosed herein, a wild type tcdC gene is confirmed by a double peak at 56±2.9° C. and 64±2.0° C. in the melting temperature analysis, while a tcdC gene that contains a deletion (e.g., a 18 bp or a 39 bp deletion) is confirmed by a single peak at 64±2.0° C. in the melting temperature analysis.

Within each thermocycler run, control samples are cycled as well. Positive control samples can amplify *C. difficile* nucleic acid control template (e.g., other than *C. difficile*) using, for example, control primers and control probes. Positive control samples can also amplify, for example, a plasmid construct containing *C. difficile* nucleic acid molecules. Such a plasmid control can be amplified internally (e.g., within the sample) or in a separate sample run side-by-side with the patients' samples. Each thermocycler run should also include a negative control that, for example, lacks *C. difficile* template DNA. Such controls are indicators of the success or failure of the amplification, hybridization and/or FRET reaction. Therefore, control reactions can readily determine, for example, the ability of primers to anneal with sequence-specificity and to initiate elongation, as well as the ability of probes to hybridize with sequence-specificity and for FRET to occur. By way of example, ATCC Accession No. 9689 represents a wild type *C. difficile*.

In an embodiment, the methods of the invention include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next. In addition, standard laboratory containment practices and procedures are desirable when performing methods of the invention. Containment practices and procedures include, but are not limited to, separate work areas for different steps of a method, containment hoods, barrier filter pipette tips and dedicated air displacement pipettes. Consistent containment practices and procedures by personnel are necessary for accuracy in a diagnostic laboratory handling clinical samples.

Conventional PCR methods in conjunction with FRET technology can be used to practice the methods of the invention. In one embodiment, a LIGHTCYCLER™ instrument is used. A detailed description of the LIGHTCYCLER™ System and real-time and on-line monitoring of PCR can be found at biochem.roche.com/lightcycler on the World Wide Web. The following patent applications describe real-time PCR as used in the LIGHTCYCLER™ technology: WO 97/46707, WO 97/46714 and WO 97/46712. The LIGHTCYCLER™ instrument is a rapid thermal cycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the LIGHTCYCLER™ thermal chamber. Addition of selected fluorescent dyes to the reaction components allows the PCR to be monitored in real time and on-line. Furthermore, the cuvettes serve as an optical element for signal collection (similar to glass fiber optics), concentrating the signal at the tip of the cuvette. The effect is efficient illumination and fluorescent monitoring of microvolume samples.

The LIGHTCYCLER™ carousel that houses the cuvettes can be removed from the instrument. Therefore, samples can be loaded outside of the instrument (in a PCR Clean Room, for example). In addition, this feature allows for the sample carousel to be easily cleaned and sterilized. The fluorometer, as part of the LIGHTCYCLER™ apparatus, houses the light source. The emitted light is filtered and focused by an epi-illumination lens onto the top of the cuvette. Fluorescent light emitted from the sample is then focused by the same lens, passed through a dichroic mirror, filtered appropriately, and focused onto data-collecting photohybrids. The optical unit currently available in the LIGHTCYCLER™ instrument (Roche Molecular Biochemicals, Catalog No. 2 011 468) includes three band-pass filters (530 nm, 640 nm, and 710 nm), providing three-color detection and several fluorescence acquisition options. Data collection options include once per cycling step monitoring, fully continuous single-sample acquisition for melting curve analysis, continuous sampling (in which sampling frequency is dependent on sample number) and/or stepwise measurement of all samples after defined temperature interval.

The LIGHTCYCLER™ can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBRGREEN I® or SYBRGOLD® (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

As described herein, amplification products also can be detected using labeled hybridization probes that take advantage of FRET technology. A common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LIGHTCYCLER™ Instrument. During FRET, the fluorescein transfers its energy to an acceptor fluorescent moiety such as LIGHTCYCLER™-Red 640 (LC™-Red 640) or LIGHTCYCLER™-Red 705 (LC™-Red 705). The acceptor fluorescent moiety then emits light of a longer wavelength, which is detected by the optical detection system of the LIGHTCYCLER™ instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target nucleic acid molecules (e.g., the number of C. difficile genomes).

Another FRET format utilizes TAQMAN® technology to detect the presence or absence of an amplification product, and hence, the presence or absence of C. difficile. TAQMAN® technology utilizes one single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target nucleic acid (i.e., the amplification product) and is degraded by the 5' to 3' exonuclease activity of the Taq Polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems, Foster City, Calif.) uses TAQMAN® technology, and is suitable for performing the methods described herein for detecting C. difficile. Information on PCR amplification and detection using an ABI PRISM® 770 system can be found at appliedbiosystems.com/products on the World Wide Web.

Molecular beacons in conjunction with FRET also can be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

It is understood that the present invention is not limited by the configuration of one or more commercially available instruments.

Articles of Manufacture/Kits

The invention further provides for articles of manufacture to detect C. difficile. An article of manufacture according to the present invention can include primers and probes used to detect C. difficile, together with suitable packaging materials. Representative primers and probes for detection of C. difficile are capable of hybridizing to tcdC nucleic acid molecules. Methods of designing primers and probes are disclosed herein, and representative examples of primers and probes that amplify and hybridize to tcdC nucleic acid molecules are provided.

Articles of manufacture of the invention also can include one or more fluorescent moieties for labeling the probes or, alternatively, the probes supplied with the kit can be labeled. For example, an article of manufacture may include a donor fluorescent moiety for labeling one of the tcdC probes and an acceptor fluorescent moiety for labeling the other tcdC probe, respectively. Examples of suitable FRET donor fluorescent moieties and corresponding acceptor fluorescent moieties are provided above.

Articles of manufacture of the invention also can contain a package insert or package label having instructions thereon for using the tcdC primers and probes to detect C. difficile in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

The invention will be further described in the following examples, which do not limit the scope of the invention described in the claims. The skilled person will understand that various additional features described above may be integrated into the methods and/or articles of manufacture/kits either together or separately.

EXAMPLES

Example 1

LIGHTCYCLER™ PCR Assay

The study protocols were approved by the Mayo Institutional Review Board. The LIGHTCYCLER™ ('LC', Roche Diagnostics) PCR detects the presence of the tcdC gene and the 18 bp and 39 bp deletions found in the tcdC gene of *C. difficile*. This gene is part of the pathogenicity locus (PaLoc) that contains the toxin A and toxin B genes along with accessory genes, tcdC and tcdD, which code for toxin expression. The tcdC gene was amplified and detected using LIGHTCYCLER™. Fifteen microliters of the "hot start" reaction mixture containing 1×LIGHTCYCLER™ FastStart DNA Master Hybridization Probes (Taq DNA polymerase, reaction buffer, dNTP mix with dUTP instead of dTTP and 10 mM MgCl$_2$), 3 mM MgCl$_2$, and 1×LC CDD Primer-Probe Set (Kit #296, TIB MolBiol, LLC, Adelphia, N.J.) was added to the LC cuvette (Table 1). Five microliters of the extracted DNA was added and the reaction was placed in the LIGHTCYCLER™. The cycling parameters were; denature template at 95° C. for 10 min, amplify template for 45 cycles of 10 sec at 95° C., 10 sec at 55° C. (single acquisition), 15 sec at 72° C., and product detection by melt analysis of 0 sec at 95° C., 20 sec at 59° C., 20 sec at 45° C. (ramp 0.2° C./sec) and 0 sec at 85° C. (ramp 0.2° C./sec, continuous acquisition). Differentiation of the toxin containing strain and the toxin strain with the deletion was accomplished by melt curve analysis (FIG. 1).

TABLE 1

Sequences used in experiments for the detection of the tcdC, toxins A and B, and the binary toxin genes of *C. difficile*

| Gene | Name | Sequence (5' → 3') | SEQ ID NO: |
|---|---|---|---|
| tcdB | TB1 | GAGCTGCTTCAATTGGAGAGA | 5 |
| tcdB | TB2 | GTAACCTACTTTCATAACACCAG | 6 |
| tcdA | TA1 | ATGATAAGGCAACTTCAGTGG | 7 |
| tcdA | TA2 | TAAGTTCCTCCTGCTCCATCAA | 8 |
| Binary | cdtApos | TGAACCTGGAAAAGGTGATG | 9 |
| Binary | cdtArev | AGGATTATTTACTGGACCATTTG | 10 |
| Binary | cdtBpos | CTTAATGCAAGTAAATACTGAG | 11 |
| Binary | cdtBrev | AACGGATCTCTTGCTTCAGTC | 12 |
| tcdC | CD1 | ACC TCA TCA CCA TCT TCA ATA AC | 1 |
| tcdC | CD2 | TCA AAA TGA AAG ACG ACG AAA | 2 |
| tcdC | CDD3 | TTC AGC CTT TTT AGC TTC TTC AGC-FL | 3 |
| tcdC | CDD4 | LC Red640-TTA CGT TGA TTT TCA GCT TCA ATA GC-PH | 4 |

Example 2

Stool Processing for PCR

A swab was inserted into the stool at various locations and swirled into a tube containing 1 ml of sterile water (approximately 1:10 stool dilution) and allowed to settle. Two hundred microliters of the supernatant was placed into a sample cartridge for DNA extraction using the MagNA Pure system with the MagNA Pure LC Total Nucleic Acid Isolation Kit.

Example 3

Verification of the LIGHTCYCLER PCR

A total of 50 strains were tested for the presence of the tcdC gene. Eleven were ATCC *C. difficile* strains, 7 were *C. difficile* clinical isolates and 26 were clinical isolates of other *Clostridium* species. Two *C. difficile* isolates provided by the CDC were also included; one isolate was Toxinotype III with the 18 bp deletion and the other isolate was the 39 bp deletion Toxinotype V isolate. An additional four isolates, two representative BI strains and two non-toxigenic strains, were provided by Dr. Dale Gerding (Hines Va. Hospital, Hines Ill. and Loyola University Medical Center, Maywood, Ill.). Specimens submitted to the Clinical Microbiology Laboratory at Mayo Clinic that were positive for *C. difficile* toxin by an antigen detection assay (Premier™ Toxins A&B, Meridian Scientific) were also used to evaluate the performance of the LIGHTCYCLER™ PCR assay. Conventional PCR also was performed on these antigen positive stool samples, amplifying the whole (~700 bp) tcdC gene using the primers described in Table 1 (Spigaglia & Mastrantonio, 2002, *J. Clin Micro.*, 40:3470-5). All tcdC gel positive specimens were sequenced on the ABI 3730 DNA sequencer and analyzed using Sequencher™ 4.2 software. Sequence alignment was performed with the Bioedit Sequence Alignment Editor software.

The probe placement in the LIGHTCYCLER™ PCR assay allows for the generation of two distinct melt temperature patterns. One melt peak identifies *C. difficile* isolates containing the deletion in the tcdC gene and the other melt peak identifies the non-deletion wild-type (FIG. 1). To determine if the toxin melt temperature pattern of the *C. difficile* isolates was correct, sequencing was performed on antigen positive, LIGHTCYCLER™ PCR positive isolates using the tcdC whole gene primers (Spigaglia & Mastrantonio, supra). The sequence results correlated with the melt temperature results differentiating the tcdC gene positive wild type (no deletion) and tcdC gene positive with the base pair deletions.

Example 4

Conventional PCR

Amplification of the whole (~700 bp) tcdC gene (Spigaglia & Mastrantonio, supra) by conventional PCR was performed on 260 antigen positive stool samples as previously described. The cycling parameters were denaturation for 5 min at 94° C., amplification consisting of 1 min at 94° C., 1 min at 50° C. and 1 min at 72° C. for 30 cycles. The presence of an amplified product was confirmed by agarose gel detection. All tcdC gel positive specimens (122/260) were sequenced on the ABI 3730 DNA sequencer and analyzed using Sequencher™ 4.2 software. Sequence alignment was performed with the Bioedit Sequence Alignment Editor software.

Example 5

Confirmation of Melt Temperature Pattern

Sequencing of the whole tcdC gene was performed on 61 antigen positive and LIGHTCYCLER™ PCR positive isolates to determine if the toxin melt temperature pattern generated by the *C. difficile* isolates was correct. After amplification of the entire tcdC gene as described above, all tcdC gel positive specimens were sequenced on the ABI 3730 DNA sequencer and analyzed using Sequencher™ 4.2 software. Sequence alignment was performed with the Bioedit Sequence Alignment Editor software. The samples sequences included the *C. difficile* isolates from the 200 stool specimens in this study along with an additional 17 samples. Twenty-two tcdC gene positive specimens with a deletion (18 with the 18-bp deletion and four with the 39 bp deletion) had a melt temperature 64° C.±2° C. and 39 tcdC gene positive specimens without a deletion showed a double hump with a melt temperature of 59.5° C.±2° C. The sequence results correlated 100% with the melt temperature results on all samples tested.

Example 6

Clinical Specimens

Two hundred stool specimens submitted to the Clinical Microbiology Laboratory at Mayo Clinic for the detection of *C. difficile* toxin were used in the comparison of test methods. The specimen criteria for use in this study were: soft or liquid stools, one specimen per patient, and fresh or frozen stools less than 48 hrs old. The Premier™ Toxins A&B was the routine test performed in the laboratory and, since these results were reported to the clinician, it was performed first. All other methods were performed within 24 hours of the first test.

Example 7

EIA, ImmunoCard, and Rapid Screening Assays

The Premier™ Toxins A&B (Meridian Bioscience Inc., Cincinnati, Ohio), the ImmunoCard® Toxins A&B (Meridian Bioscience Inc., Cincinnati, Ohio), the Xpect® *C. difficile* Toxin A/B (Remel Inc., Lenexa, Kans.), and the Triage® *C. difficile* Panel test (Biosite Diagnostics, San Diego, Calif.) were performed on the 200 comparative test specimens according to the manufacturers' instructions.

Example 8

Culture for *C. difficile*

Anaerobic culture was performed on the 200 test specimen stools by plating the specimens onto pre-reduced Fastidious Anaerobic Agar with Sheep Blood (FAASB) and Taurocholate, Cycloserine, Cefoxitin, Fructose Agar (TCCFA). The TCCFA plate was inoculated with fresh stool. The FAASB was inoculated with 10 µl of stool sample after alcohol shock (equal volumes of 95% ethanol to stool). After anaerobic incubation for 2 days at 35° C., presumptive *C. difficile* colonies were identified by both biochemical and morphologic characteristics and 16S sequencing (Applied Biosystems MicroSeq®).

Example 9

Agar Dilution MIC Testing of Anaerobes

Moxifloxicin susceptibility testing by agar dilution was performed on all *C. difficile* culture positive isolates. Growth from subculture plates was suspended in pre-reduced Schaedler's broth to McFarland 0.5 turbidity. A Steers replicator seed block was used to inoculate the moxifloxicin plate from lowest to highest dilution. The inoculated media was incubated under anaerobic conditions for 48 hours before endpoint determination was read. The testing was performed and interpreted as defined in CLSI document M11-A7.

Example 10

Confirmation of Toxin Production

All *C. difficile* culture positive specimens were tested for the presence of toxin by the LIGHTCYCLER™ PCR and conventional PCR using primers specific for toxin A (tcdA) and toxin B (tcdB) gene as previously described (Spigaglia & Mastrantonio, supra). The sequences of the primers used for amplification are found in Table 1 and the cycling parameters were the same as listed above for the amplification of the entire tcdC gene. There was total agreement between the two PCR methods, thus verifying the use of the LIGHTCYCLER™ PCR method for detection of toxin production by culture isolates.

Example 11

Presence of the Binary Toxin

*C. difficile* LIGHTCYCLER™ PCR positive specimens were examined for the production of the actin-specific ADP-ribosyltransferase or binary toxin. The primer sequences are listed in Table 1. The cycling parameters and reaction mixture were followed as previously described (Terhes et al, 2004, *J. Clin. Micro.*, 42:4316-4318).

Example 12

Results

A total of 200 stool specimens were studied by the comparative methods. *C. difficile* was isolated from 49 specimens by culture and 44 of these were confirmed as toxigenic ("toxigenic culture") using the LIGHTCYCLER™ PCR assay and another assay detecting the toxin A and B genes. Using toxigenic culture as the "gold standard", the sensitivities, specificities, positive and negative predictive values, respectively, of the assays were: Premier™ Toxins A&B 48%, 98%, 88, 87%; ImmunoCard® Toxins A&B 48%, 99%, 91%, 87%; Xpect® *C. difficile* Toxin A/B 48%, 84%, 46%, 85%; Triage *C. difficile* Panel (for toxin A) 33%, 100%, 100%. 85%; LC PCR 86%, 97%, 90%, 96%. (Table 2).

TABLE 2

Comparison of *Clostridium difficile* toxin immunoassays and real-time PCR results with toxogenic culture

| Assay | | No. of Specimens | | Toxigenic Culture[a] Comparison to toxigenic culture | | | |
|---|---|---|---|---|---|---|---|
| | | + | − | Sensitivity | Specificity | PPV | NP |
| Premier Toxins A & B | + | 21 | 3 | 48% | 98% | 88% | 87% |
| | − | 23 | 153 | | | | |
| Xpect® *C. difficile* A/B | + | 21 | 25 | 48% | 84% | 46% | 85% |
| | − | 23 | 131 | | | | |
| Immunocard® Toxins A & B | + | 21 | 2 | 48% | 99% | 91% | 87% |
| | − | 23 | 154 | | | | |
| Triage *C. difficile* Panel | + Toxin A | 14 | 0 | 33% | 100% | 100% | 85% |
| | − | 29 | 158 | | | | |
| LIGHTCYCLER™ Real-time PCR | + | 38 | 4 | 86% | 97% | 90% | 96% |
| | − | 6 | 152 | | | | |

[a]Anaerobic culture was performed on the 200 test specimens stools by plating the specimens onto pre-reduced Fastidious Anaerobic Agar with Sheep Blood (FAASB) and Taurocholate, Cycloserine, Cefoxitin, Fructose Agar (TCCFA). All *C. difficile* culture positive specimens were tested for the presence of toxin by the LC PCR and conventional PCR using primers specific for toxin A (tcdA) and toxin B (tcdB) gene as previously described (Spigaglia & Mastrantonio, supra).

If the PCR assay was used as the "gold standard", the sensitivities of the toxin immunoassays were: Premier™ and ImmunoCard® both 52%; Xpect® 50%; and Triage, toxin A 33%. Specificities were 84%-100%. Thus, in comparison to either PCR or toxigenic culture, the sensitivities of the toxin immunoassays were very low. The specificities, however, were quite acceptable. The LIGHTCYCLER™ PCR tcdC assay was both sensitive and specific in comparison to toxigenic culture and the predictive values were both ≧90%. There were 4 specimens which were PCR positive but were not detected by culture. In these cases, the concentration of gene target was very low as evidenced by detection by melting curve analysis only with no amplicon detectable by crossing points above the baseline curve on the graph plot. Presumably, then, the very sensitive molecular assay was able to detect low concentrations of target nucleic acid when there were too few organisms present to detect by culture. The Triage GDH assay detected only 67% (33 of 49) of the culture positive *C. difficile* isolates and 79% (33 of 42) of the culture positive isolates which were toxin producers. In this study, then, the GDH assay was not a sensitive alternative to culture for *C. difficile*.

Base pair (bp) deletions in the tcdC gene of 18 or 39 bp (confirmed by sequence analysis) were detected in 12 of the 13 LIGHTCYCLER™ PCR deletion positive specimens (Table 3). One sample with the deletion produced a poor sequence, so the type of deletion could not be determined. Nine samples had the 18 bp deletion, while 3 had the 39 bp deletion. The sequences generated were similar to that of an isolate identified as a BI strain by restriction enzyme analysis in the laboratory of Dale N. Gerding (Hines Va. Hospital, Hines and Loyola University Medical Center, Maywood, Ill.; personal communication) and also correlated with two *C. difficile* isolates provided by the CDC; one isolate was Toxinotype III with the 18 bp deletion and the other isolate was the 39 bp deletion Toxinotype V isolate.

TABLE 3

Results of other tests performed on the *C. difficile* culture positive and LIGHTCYCLER™ PCR tcdC gene positive specimens

| LIGHTCYCLER PCR | Binary Toxin Present | | Type of tcdC Deletion[a] Demonstrated | | Susceptibility to Moxifloxicin | | | |
|---|---|---|---|---|---|---|---|---|
| | Yes | No | 18 bp | 39 bp | S ≦ 2 | I = 4 | R > 8 | NG |
| bp deletions demonstrated | 11 | 2 | 9 | 3 | 7 | 0 | 6 | |
| no deletions demonstrated | 3 | 28 | | | 20 | 2 | 7 | 2 |
| Total | 14 | 30 | | | 32 | 2 | 13 | 2 |

[a]The sequence results for one of the specimens was poor. Therefore, only results on 12 of the 13 specimens with the tcdC deletion were available
S = susceptible, I = intermediate, R = resistant, NG = no growth for susceptibility testing.
Anaerobic susceptibilities performed by agar dilution method (CLSI document M11-A5)

Forty-nine specimens were positive for *C. difficile* by culture and 44 of those had toxin production confirmed by LIGHTCYCLER™ PCR assay for tcdC. To confirm that the LIGHTCYCLER™ PCR described herein was accurately detecting toxin production by these culture isolates, all 49 of these specimens were tested by a second PCR assay specific for toxin A (tcdA) and toxin B (tcdB). All 44 of the LIGHTCYCLER™ PCR toxin positive culture isolates were positive for the tcdA and tcdB genes (36 both toxins A and B, 5 toxin A only, and 3 toxin B only). Five culture isolates, which were LIGHTCYCLER™ PCR negative for tcdC, were also negative for the tcdA and tcdB genes. These results indicate that PCR detection of the tcdC negative regulator gene is equivalent to detection of the tcdA and tcdB genes for the demonstration of the presence of toxins A and/or B.

Other experiments performed on the 49 culture positive specimens were binary toxin gene detection by conventional PCR and moxifloxicin susceptibility testing by agar dilution (Table 3). Fourteen *C. difficile* culture positive, LIGHTCYCLER™ PCR positive specimens contained the binary toxin gene and 30 were binary toxin gene negative. Eleven of thirteen (85%) specimens with a deletion in the tcdC contained the gene for the binary toxin while only 9% of the specimens without the deletion contained the binary toxin gene. The susceptibility testing of moxifloxicin by agar dilution was performed on all 49 *C. difficile* culture positive isolates. Thirty-two of the culture positive isolates (65%) were susceptible to moxifloxicin at $\leq 2$ μg/mL, two (4%) were intermediate at 4 μg/mL, and 13 (26%) were resistant to moxifloxicin at $\geq 8$ μg/mL. Although there were only 13 specimens with the tcdC gene deletions in the 200 specimens tested, 46% of these showed resistance to moxifloxicin.

Example 13

Summary and Interpretation of Results

In summary, using culture with toxin detection as the comparative method (Table 1), the toxin detecting immunoassays lacked sensitivity (32%-48%) whereas the LIGHTCYCLER™ PCR was both sensitive (86%) and specific (97%). Using the LIGHTCYCLER™ PCR as the comparative method (Table 2), the immunoassays sensitivity were between 33%-52%, while the culture (with toxin confirmation) was sensitive (90%) and specific (96%).

49 stool specimens were positive for *C. difficile* by conventional culture and also be 16S sequence analysis: 44 of these stools were confirmed toxin-positive by PCR from a broth culture of an isolated colony; and 5 isolates were *C. difficile* non-toxin producers.

The 44 toxin positive stools were also tested by a conventional PCR detecting toxin A and B: 36 were positive for both toxins A and B; 5 were positive for toxin A only; and 3 were positive for toxin B only.

42 stool specimens were LIGHTCYCLER™ PCR-positive and *C. difficile* culture/toxin-positive: 6 stools were LIGHTCYCLER™ PCR-negative and culture/toxin-positive (stool inhibition was not investigated); and 4 stools were LIGHTCYCLER™ PCR-positive and culture/toxin-negative. The LIGHTCYCLER™ PCR-positives were positive by melting temperature only, indicating that the concentration of the nucleic acid in the stool was very low. In addition, 13 of the LIGHTCYCLER™ PCR-positive/toxin-positive specimens contained the 18 or 39 bp deletions in the tcdC gene, indicating the presence of a hyper-producing toxin strain.

The Triage *C. difficile* panel detects the presence of the "common antigen" and toxin A. The presence of both the "common antigen" and toxin A was considered to be a positive result for these purposes. Looking at only the "common antigen" results, the Triage was sensitive (79%) and specific (98%) in comparison to culture (without toxin detection) for the detection of *C. difficile*.

The LIGHTCYCLER™ PCR is a rapid method for diagnosis of *C. difficile* associated diarrhea (CDAD) and pseudomembranous colitis (PMC). The test can be completed in less than 4 hours (including extraction and detection) compared to 48 hours or more for culture. The LIGHTCYCLER™ PCR is also sensitive and specific for diagnosis of CDAD and PMC when compared to commercial enzyme immunoassays. In addition, the LIGHTCYCLER™ PCR has the ability to detect *C. difficile* toxin hyper-producing strains, as 13 strains having base pair deletions associated with *C. difficile* toxin hyper-production were detected using LIGHTCYCLER™ PCR.

It is noted that culturing *C. difficile* (with toxin detection) correlated best with LIGHTCYCLER™ PCR for detecting positive specimens. The EIA, Immunocard, and Rapid assays were variable in their performance and lacked sensitivity in comparison to culture (with toxin detection) and LIGHTCYCLER™ PCR. The Triage common antigen assay was specific for the detection of *C. difficile* compared to culture (without toxin detection).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting the presence or absence of *C. difficile* in a biological sample from an individual, said method comprising:

performing at least one cycling step, wherein a cycling step comprises an amplifying step and a hybridizing step, wherein said amplifying step comprises contacting said sample with a pair of tcdC primers to produce a tcdC amplification product if a tcdC nucleic acid molecule is present in said sample, wherein said pair of tcdC primers comprises a first tcdC primer and a second tcdC primer, wherein said first tcdC primer comprises the sequence 5'-ACC TCA TCA CCA TCT TCA ATA AC-3' (SEQ ID NO:1), and wherein said second tcdC primer comprises the sequence 5'-TCA AAA TGA AAG ACG ACG AAA-3' (SEQ ID NO:2), wherein said hybridizing step comprises contacting said sample with a pair of tcdC probes, wherein the members of said pair of tcdC probes hybridize to said tcdC amplification product within no more than five nucleotides of each other, wherein a first tcdC probe of said pair of tcdC probes is labeled with a donor fluorescent moiety and said second tcdC probe of said pair of tcdC probes is labeled with a corresponding acceptor fluorescent moiety; and detecting the presence or absence of fluorescence resonance energy transfer (FRET) between said donor fluorescent moiety of said first tcdC probe and said acceptor fluorescent moiety of said second tcdC probe, wherein the presence of FRET is indicative of the presence of *C. difficile* in said sample, and wherein the absence of FRET is indicative of the absence of *C. difficile* in said sample.

2. The method of claim 1, wherein said first tcdC probe comprises the sequence 5'-TTC AGC CTT TTT AGC TTC TTC AGC -3' (SEQ ID NO:3), and wherein said second tcdC probe comprises the sequence 5'-TTA CGT TGA TTT TCA GCT TCA ATA GC-3' (SEQ ID NO:4).

3. The method of claim 1, wherein the members of said pair of tcdC probes hybridize within no more than two nucleotides of each other.

4. The method of claim 1, wherein the members of said pair of tcdC probes hybridize within no more than one nucleotide of each other.

5. The method of claim 1, wherein said donor fluorescent moiety is fluorescein.

6. The method of claim 1, wherein said corresponding acceptor fluorescent moiety is selected from the group consisting of LC-Red 640, LC-Red 705, Cy5, and Cy5.5.

7. The method of claim 1, wherein said detecting comprises exciting said sample at a wavelength absorbed by said donor fluorescent moiety and visualizing and/or measuring the wavelength emitted by said corresponding acceptor fluorescent moiety.

8. The method of claim 1, wherein said detecting comprises quantitating said FRET.

9. The method of claim 1, wherein said detecting is performed after each cycling step.

10. The method of claim 1, wherein said detecting is performed in real time.

11. The method of claim 1, further comprising determining the melting temperature between one or both of said tcdC probe(s) and said tcdC amplification product, wherein said melting temperature confirms said presence or said absence of said *C. difficile*.

12. The method of claim 11, wherein, when said determining results in two melting temperatures, the *C. difficile* is wild type.

13. The method of claim 11, wherein, when said determining results in one melting temperature, the *C. difficile* is a mutant that contains a genetic deletion.

14. The method of claim 13, wherein the genetic deletion is an 18 by deletion or a 39 by deletion in the tcdC nucleic acid molecule.

15. The method of claim 1, further comprising: preventing amplification of a contaminant nucleic acid.

16. The method of claim 15, wherein said preventing comprises performing said amplifying step in the presence of uracil.

17. The method of claim 16, wherein said preventing further comprises treating said sample with uracil-DNA glycosylase prior to a first amplifying step.

18. The method of claim 1, wherein said biological sample is selected from the group consisting of a stool sample.

19. The method of claim 1, wherein said cycling step is further performed on a control sample.

20. The method of claim 19, wherein said control sample comprises said tcdC nucleic acid molecule.

21. The method of claim 1, wherein said cycling step uses a pair of control primers and a pair of control probes, wherein said control primers and said control probes are other than said tcdC primers and tcdC probes, wherein said amplifying step produces a control amplification product, wherein said control probes hybridize to said control amplification product.

22. A method for detecting the presence or absence of *C. difficile* in a biological sample from an individual, said method comprising:
    performing at least one cycling step, wherein a cycling step comprises an amplifying step and a hybridizing step, wherein said amplifying step comprises contacting said sample with a pair of tcdC primers to produce a *C. difficile* tcdC amplification product if a tcdC nucleic acid molecule is present in said sample, wherein said pair of tcdC primers comprises a first tcdC primer and a second tcdC primer, wherein said first tcdC primer comprises the sequence 5'-ACC TCA TCA CCA TCT TCA ATA AC-3' (SEQ ID NO:1), and wherein said second tcdC primer comprises the sequence 5'-TCA AAA TGA AAG ACG ACG AAA-3' (SEQ ID NO:2), wherein said hybridizing step comprises contacting said sample with a tcdC probe, wherein the tcdC probe is labeled with a donor fluorescent moiety and a corresponding acceptor fluorescent moiety; and
    detecting the presence or absence of fluorescence resonance energy transfer (FRET) between said donor fluorescent moiety and said acceptor fluorescent moiety of said tcdC probe,
    wherein the presence or absence of fluorescence is indicative of the presence or absence of *C. difficile* in said sample.

23. The method of claim 22, wherein said amplifying step employs a polymerase enzyme having 5' to 3' exonuclease activity.

24. The method of claim 23, wherein said donor and corresponding acceptor fluorescent moieties are within no more than 5 nucleotides of each other on said probe.

25. The method of claim 24, wherein said acceptor fluorescent moiety is a quencher.

26. The method of claim 22, wherein said tcdC probe comprises a nucleic acid sequence that permits secondary structure formation, wherein said secondary structure formation results in spatial proximity between said first and second fluorescent moiety.

27. The method of claim 26, wherein said second fluorescent moiety is a quencher.

28. A method for detecting the presence or absence of *C. difficile* in a biological sample from an individual, said method comprising:
    performing at least one cycling step, wherein a cycling step comprises an amplifying step and a dye-binding step, wherein said amplifying step comprises contacting said sample with a pair of tcdC primers to produce a tcdC amplification product if a tcdC nucleic acid molecule is present in said sample, wherein said pair of tcdC primers comprises a first tcdC primer and a second tcdC primer, wherein said first tcdC primer comprises the sequence 5'-ACC TCA TCA CCA TCT TCA ATA AC-3' (SEQ ID NO:1), and wherein said second tcdC primer comprises the sequence 5'-TCA AAA TGA AAG ACG ACG AAA-3' (SEQ ID NO:2), wherein said dye-binding step comprises contacting said tcdC amplification product with a double-stranded DNA binding dye; and
    detecting the presence or absence of binding of said double-stranded DNA binding dye into said amplification product,
    wherein the presence of binding is indicative of the presence of *C. difficile* in said sample, and wherein the absence of binding is indicative of the absence of *C. difficile* in said sample.

29. The method of claim 28, wherein said double-stranded DNA binding dye is ethidium bromide.

30. The method of claim 28, further comprising determining the melting temperature between said tcdC amplification product and said double-stranded DNA binding dye, wherein said melting temperature confirms said presence or absence of said *C. difficile*.

* * * * *

UNITED STATES PATENT AND TRADEMARK OFFICE
CERTIFICATE OF CORRECTION

PATENT NO.        : 8,101,362 B2                          Page 1 of 1
APPLICATION NO.   : 12/367014
DATED             : January 24, 2012
INVENTOR(S)       : Franklin R. Cockerill, III It is certified that error appears in the above-identified patent and that said Letters Patent is hereby corrected as shown below:

Column 27, line 19 (Claim 14), please delete "an 18 by deletion or a 39 by deletion in the tcdC nucleic acid" and insert --an 18 bp deletion or a 39 bp deletion in the tcdC nucleic acid-- therefor.

Signed and Sealed this
Tenth Day of July, 2012

David J. Kappos
*Director of the United States Patent and Trademark Office*